(12) United States Patent
Komerska et al.

(10) Patent No.: US 6,566,576 B1
(45) Date of Patent: May 20, 2003

(54) HYDROCOLLOID FOAM MEDICAL DRESSINGS AND METHOD OF MAKING THE SAME

(76) Inventors: James F. Komerska, 120 Cornwall Dr., Chalfont, PA (US) 18914; Michael J. Derr, 414 Shipwrighter Way, Lansdale, PA (US) 19446; Wayne Celia, 242 Purdue Ct., Paramus, NJ (US) 07652

( * ) Notice: Subject to any disclaimer, the term of this patent is extended or adjusted under 35 U.S.C. 154(b) by 0 days.

(21) Appl. No.: 09/477,439

(22) Filed: Jan. 4, 2000

(51) Int. Cl.[7] ............................................... A61F 13/00
(52) U.S. Cl. ............................ 602/46; 602/43; 602/48
(58) Field of Search ....................... 602/41–59; 128/888, 128/889; 604/304

(56) References Cited

U.S. PATENT DOCUMENTS

| | | | |
|---|---|---|---|
| 4,292,214 A | 9/1981 | Blount | 260/9 |
| 4,624,868 A | 11/1986 | Muller | 427/384 |
| 4,948,575 A | 8/1990 | Cole et al. | 424/44 |
| 5,210,117 A | 5/1993 | Lee et al. | 524/28 |
| 5,256,477 A | 10/1993 | Mahoney | 428/283 |
| 5,470,576 A | 11/1995 | Patel | 424/445 |
| 5,602,183 A | 2/1997 | Martin et al. | 514/724 |
| 5,652,274 A | 7/1997 | Martin | 514/724 |
| 5,653,699 A | 8/1997 | Reed et al. | 604/307 |
| 5,662,624 A | 9/1997 | Sundstrom et al. | 604/291 |
| 5,674,524 A | 10/1997 | Scherr | 424/445 |
| 5,681,579 A * | 10/1997 | Freeman | 424/448 |
| 5,716,337 A | 2/1998 | McCabe et al. | 602/49 |
| 5,763,067 A | 6/1998 | Bruggemann et al. | 428/317.9 |
| 5,763,335 A | 6/1998 | Hermann | 442/370 |
| 5,792,090 A | 8/1998 | Ladin | 602/48 |
| 5,836,970 A | 11/1998 | Pandit | 606/213 |
| 5,914,125 A * | 6/1999 | Andrews et al. | 424/443 |
| 5,925,009 A * | 7/1999 | Mahoney et al. | 602/44 |

OTHER PUBLICATIONS

*Carington Wound Care Products* (visited Nov. 23, 1998) <http://www.carringtonlabs.com/wound6.html>.

Johnson & Johnson Medical, Inc. *Introd Sof–Foam & Trade; Dressing* (visited Nov. 23, 1998) <htpp://www.woundcare.org/newsvol2n3/pr11/htm>.

J.H. Scurr, BSc, FRCS; L.A. Wilson, RN; P.D. Coleridge Smith, *A Comparison of the Effects of Semipermeable Foam and Film Secondary Dressings Over Alginate Dressings on the Healing and Management of Venous Ulcers* (visited Nov. 23, 1998) <http://www.dowhickam.creprints/foamandfilm_onulcers.html>.

Michael Moran, ScD, PT and Mark Brimer, MBA, PT, *Sorbsan—A Topical Wound Care Dressing: A Literature Review* (visited Nov. 23, 1998) <http://www.dowhickam.creprints/ topicalwounddressing.html>.

* cited by examiner

Primary Examiner—Kim M. Lewis
(74) Attorney, Agent, or Firm—Lerner, David, Litttenberg, Krumholz & Mentlik, LLP

(57) ABSTRACT

Foam wound dressings for medical and veterinary use are disclosed, along with methods for making the same. The wound dressings contain a hydrophilic polyurethane foam matrix having at least one hydrocolloid absorptive material integrally and generally uniformly dispersed throughout that improves the absorptive properties of the wound dressing. The foam wound dressings are formed from a polymerized combination of an aqueous mixture having at least one hydrocolloid absorptive material with a hydrophilic urethane prepolymer in a predetermined ratio.

17 Claims, 1 Drawing Sheet

HYDROCOLLOID FOAM MEDICAL DRESSINGS AND METHOD OF MAKING THE SAME

BACKGROUND OF THE INVENTION

The present invention relates generally to medical dressings and to methods of making the same, and more specifically to foam medical dressings having hydrocolloid absorptive agents incorporated in and formed integrally with at least one formed foam layer of the medical dressings to provide improved fluid uptake, retention and removal properties.

Hydrocolloids are well known and widely used in wound dressings. These agents are particularly suitable for wound dressings because of their strong absorptive properties and because they are biocompatible and noncytotoxic. In addition to the absorptive properties of hydrocolloids, various hydrocolloids, such as calcium alginates, have been reported to promote wound healing by stimulating the platelet activation and whole-blood coagulation.

Hydrocolloids are generally incorporated in wound dressings in the form of a fibrous-knitted layer. For example, U.S. Pat. No. 5,653,699 discloses a syproadsorbent-layered system in which a fibrous mat of hydrocolloids is positioned as an island on a film adhesive structure. U.S. Pat. Nos. 5,470,576, 5,792,090, and 5,764,524 also describe hydrocolloid dressings in which the hydrocolloid absorbent material is either impregnated after the fibrous dressing base is formed or is layered into the fibrous layer.

Nonfibrous alginate wound dressings are also known. U.S. Pat. No. 4,948,575, for example, describes a water-insoluble alginate hydrogel foam wound dressing that is formed in place in the wound cavity or on the wound surface from a reactive composition that foams as it gels. U.S. Pat. No. 4,393,080 also discloses a gel wound dressing that is formed of a water-soluble hydrogel of alkali metal alginate and glycerin.

More recently, U.S. Pat. No. 5,836,970 describes a chitosan/alginate foam for use as a wound dressing in which the foam is formed by admixing chitosan and alginate with a minimal amount of a solvent and then freeze drying the foam product.

SUMMARY OF THE INVENTION

The present invention provides an improved medical and wound dressing wherein during formation of the medical and wound dressing, at least one hydrocolloid is added directly to an aqueous polymerization mixture to provide at least one formed foam layer in the medical and wound dressing with the hydrocolloid absorptive agent or agents, as the case may be, integrally dispersed generally uniformly throughout the at least one formed foam layer of the wound dressing. Other ingredients may also be added to provide additional advantages to the improved medical or wound dressing.

Accordingly, it is an aspect of the present invention to provide a foam medical dressing that has improved fluid uptake and retention properties. The medical dressing includes a monolithic, polyurethane foam layer with hydrocolloid absorptive agents incorporated and formed integrally therewith. The foam layer comprises the integrated reaction products of an aqueous mixture of at least one hydrocolloid absorptive agent and hydrophilic polyurethane prepolymer. In accordance with the present invention, a prepolymer is defined as any monomeric, oligomeric or polymeric material or resin capable of undergoing further polymerization and curing into a polymeric matrix.

The incorporation of the hydrocolloid absorptive agents into the aqueous mixture for the hydrophilic polyurethane prepolymer prior to foam formation imparts certain improved and distinct properties to the formed medical dressing. Most notably, the incorporation of the hydrocolloid absorptive agents prior to foam formation "locks in" a substantial portion of the hydrocolloid material, thereby improving the absorption capacity of the formed foam without the need for an additional absorptive layer or post foam formation processing. The addition of the hydrocolloid absorptive agents prior to foam formation also imparts uniform exudate absorption properties and substantially reduces swelling of the formed foam upon liquid uptake which prevents the foam from losing its mechanical integrity when it becomes wet. In addition to the improved absorption properties, the incorporation of hydrocolloids prior to foam formation also imparts a slippery surface on the foam, which prevents adherence of the medical dressing to the wound bed.

DETAILED DESCRIPTION

Figure 1:
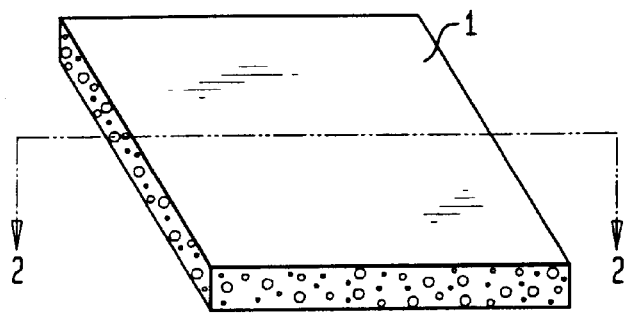
FIG. 1 is a perspective view of the foam cover layer of the wound dressing of the present invention.
Figure 2:
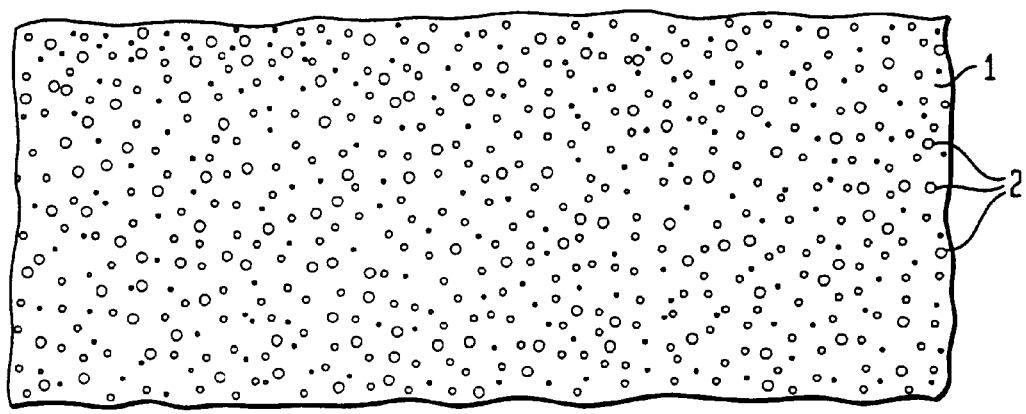
FIG. 2 is an enlarged cross-section taken on line 2—2 of FIG. 1.
Figure 3:
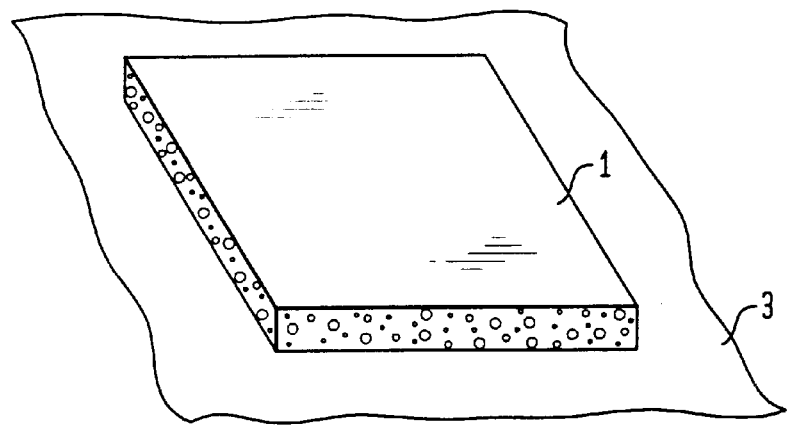
FIG. 3 is a perspective view of the foam cover layer and a film backing.

As shown in FIGS. 1, 2 and 3, the medical dressings of the present invention includes at least one monolithic, polyurethane foam layer generally designated 1 which is formed by polymerizing an aqueous mixture having one or more hydrocolloid absorptive agents with an aqueous mixture of a hydrophilic polyurethane prepolymer, in a predetermined ratio, so that the polymerization of the polyurethane foam forms a matrix binder for the one or more hydrocolloid absorptive agents. As shown in FIG. 2, the hydrocolloid absorptive agents generally designated 2 are thereby incorporated and integrally dispersed directly into the matrix of the formed foam.

The term "hydrocolloid absorptive agent" as used in accordance with the present invention includes natural, chemically modified, and synthetic hydrocolloids. Suitable hydrocolloids include, but are not limited to, natural gums such as arabic gum, ghatti gum, karaya gum, tragacanth gum, guar gum, locust bean gum and acacia gum; seaweed extracts such as agar, algin, alginate salts and carrageenin; cereal gums; starches; fermentation or microbial gums such as dextran gum and xanthan gum; pectins; gelatins; casein; and collagens. Modified forms of the hydrocolloids may also be used, including, for example, the oxidized, acetylated, carboxylated, esterified, methylated, aminated, etherated, sulfated, borated and phosphated derivatives of the hydrocolloid absorptive agents. Suitable synthetic gums include polyvinylpyrrolidone, low methoxyl pectin, propyleneglycol alginates, carboxymethyl locust bean gum and carboxymethyl guar gum.

The medical dressings of the present invention are formed by metering and mixing an aqueous mixture including adequate water and at least one hydrocolloid absorptive agent with a predetermined ratio of hydrophilic urethane prepolymer to provide a prepolymerizing mixture. The hydrocolloid absorptive agents are included in the aqueous phase in an amount of about 0.5% to about 20.0% by weight. More preferably, the hydrocolloid absorptive agents are included in an amount of about 5% to about 15% by weight. Preferably, the hydrophilic urethane prepolymer is included in the aqueous phase in an amount of about 25% to about 45% by weight. Suitable surfactants, such as, for example, BASF Pluronic L 92 or BASF Pluronic F-88 (BASF, Mt. Olive, N.J.), may preferably be added to the aqueous phase. Preferably surfactants may be added in an amount of about 0.2% to about 25.0% wet weight of the aqueous phase. More preferably surfactants may be added in an amount of about 0.5% to about 2.5% wet weight of the aqueous phase.

The hydrophilic urethane prepolymer materials used in the medical dressings of the present invention are available in the commercial marketplace, and include, for example, Bipol 6, available from Mace Adhesives and Coatings, and HYPOL from W. R. Grace. General procedures for the preparation and formation of such prepolymers can be found in Polyurethanes: Chemistry and Technology by J. H. Saunders and K. C. Frisch published by John Wiley & Sons, New York, N.Y., at Vol. XVI Part 2, High Polymer Series, "Foam Systems", pages 7–26, and "Procedures for Preparation of Polymers", pages 26, et seq., which are hereby incorporated by reference herein.

The medical and wound dressings of the present invention can also include various combinations of other ingredients without departing from the scope of the present invention, including, for example, medicaments, soaps, disinfecting and sterilizing agents, odor management agents, hemostatic agents, proteins, enzymes and nucleic acids. Preferably these agents may also be incorporated directly and dispersed throughout the prepolymerization aqueous mixture and are thereby incorporated into the foam matrix. Alternatively these other ingredients may be incorporated into the dressing by absorbing them into the formed foam cover layer following the polymerization reaction by affixing to the formed medical and wound dressings, by any suitable means, an additional layer incorporating such other ingredients, as will be understood by those skilled in the art.

Suitable medicaments, soaps, disinfecting and sterilizing agents, proteins, and enzymes are provided in the commercial market place by a myriad of suppliers and include those which aid recovery of wounds. Preferably, the medicaments include antifungal agents, antibacterial agents, angiogenesis promoting agents and the like. More preferred medicaments include antifungal agents such as metronidazole and antibacterial agents such as chlorhexidine. Any suitable soap, disinfecting and sterilizing agent may be used. A preferred disinfecting and sterilizing agent includes hydrogen peroxide. Suitable proteins and enzymes include those which aid in wound recovery such as fibrin sealants and angiotensins, as described in U.S. Pat. Nos. 5,962,420 and 5,955,430, hereby incorporated by reference herein.

After blending and mixing the combination of the aqueous mixtures and hydrophilic urethane prepolymer, the polymerizing foam composition is preferably deposited on a releasable bottom sheet material on a movable carrier. The upper surface of the polymerizing composition is then covered with a releasable top sheet material and advanced along the moveable carrier for sizing of the foam to the desired thickness and until the foam is tack free. The releasable top and bottom sheets are then sequentially removed. When polymerization is complete, residual water may be driven off by drying the foam. Preferably, the drying is done in a drying unit at a temperature of about 200° F.

Drying may also be performed at lower temperatures under reduced pressures.

The medical dressings of the present invention may be formed to have any desired thickness or shape. The foam layer is preferably relatively thin. More preferably, the foam layer should have a thickness of about 1 mm to about 10 mm, and more preferably about 1.5 mm to about 6.0 mm.

Various forms of the preformed foam medical dressings of the present invention are contemplated. In a preferred embodiment, the medical dressing is an occlusive dressing which includes the foam layer and a biocompatible backing sheet or layer 3 which surrounds the foam layer. Any suitable biocompatible backing may be used, however, preferably, the backing is moisture vapor permeable. As shown in FIG. 3, in a preferred embodiment, the backing layer 3 is a hydrophilic polyurethane film which has been laminated to the foam layer 1. The backing layer 3 may extend beyond the foam layer 1 for contact with the skin of the patient.

Suitable noncytotoxic and substantially nonallergenic adhesives and/or tapes may be used to apply the medical dressings of the present invention to the skin of a patient. In a preferred embodiment, the adhesive is applied to all or a portion of the backing layer which extends beyond the foam cover layer. Preferably, the adhesives and/or tapes include those formed from polymers containing hydrophilic groups, such as hydroxyl, carboxyl, amine, amide, ether and alkoxy. More preferably, the adhesive is a pressure-sensitive acrylic adhesive. Such adhesive and tapes are well known in the art and therefore are-not more fully described.

It is to be understood that the above-detailed description of the preferred embodiment of the invention is provided by way of example only. Various details of the design, construction and composition may be modified without departing from the scope of the invention as set forth in the claims. In addition, the invention will be further described by reference to the following detailed examples. These examples are merely illustrative and not limitative of Applicants' invention in any way.

EXAMPLE 1

An aqueous mixture comprising 4% karaya gum, water and a suitable surfactant is combined in a 60:40 ratio with hydrophilic prepolymer to form the foam.

| | |
|---|---|
| Purified water: | 190.38 parts |
| Karaya Gum: | 8.00 parts |
| BASF Pluronic L 92: | 1.60 parts |
| BASF Pluronic F-88: | 0.02 parts |

Mixing was done at room temperature. L-92 and F-88 were added to water and mixed until they were completely dispersed in the water. Speed of the mixture was increased and the gum was added slowly into the vortex. Mixing was complete when the mixture was smooth (no gel particles visible). When mixing was complete, the aqueous was combined with hydrophilic prepolymer as follows

| | |
|---|---|
| Above aqueous: | 200.00 parts |
| Hypol prepolymer: | 133.33 parts |

The combination was mixed in a high speed mixing vessel until the parts were homogeneous. The combination was then poured and sized using suitable releasable substrate or substrates and allowed to cure until the foam structure was stable.

EXAMPLE 2

An aqueous mixture comprising 2% locust bean gum, water and a suitable surfactant was combined in a 60:40 ratio with hydrophilic prepolymer to form foam.

| Purified water: | 194.38 parts |
|---|---|
| Locust Bean Gum: | 4.06 parts |
| BASF Pluronic L 92: | 1.60 parts |
| BASF Pluronic F-88: | 0.02 parts |

Mixing was done at room temperature. L-92 and F-88 were added to the water and mixed until they were completely dispersed in the water. Speed of the mixture was increased and the gum was added slowly into the vortex. Mixing was complete when the mixture was smooth (no gel particles visible). The aqueous was then combined with hydrophilic prepolymer as follows:

| Above aqueous: | 200.00 parts |
|---|---|
| Hypol prepolymer: | 100.00 parts |

The combination was mixed in a high speed mixing vessel until the parts were homogeneous. It was then poured and sized using suitable releasable substrate or substrates and allowed to cure until foam structure was stable.

EXAMPLE 3

Comprising 4% alginate, water and a suitable surfactant was combined in a 60:40 ratio with hydrophilic prepolymer to form foam.

| Purified water: | 190.38 parts |
|---|---|
| Kelco LVCR Alginate: | 8.00 parts |
| BASF Pluronic L 92: | 1.60 parts |
| BASF Pluronic F-88: | 0.02 parts |

Mixing was done at room temperature. L-92 and F-88 were added to the water and mixed until they are completely dispersed in the water. Speed of the mixture was increased and the gum was added slowly into the vortex. Mixing was complete when the mixture was smooth (no gel particles visible). When mixing was complete, the aqueous was combined with hydrophilic prepolymer as follows:

| Above aqueous: | 200.00 parts |
|---|---|
| Hypol prepolymer: | 133.33 parts |

The combination was mixed in a high speed mixing vessel until the parts are homogeneous. It was then poured and sized using suitable releasable substrate or substrates and allowed to cure until foam structure is stable.

EXAMPLE 4

A test was designed to measure the amount of water retained in the foam after squeezing. With the foam containing the hydrocolloid additive, a noticeable increase in the amount of retained water was observed. Results of this test using the average of five samples are as follows:

| Sample | Dry weight | Weight after squeezing |
|---|---|---|
| Standard Hydrophilic foam | 2.34 grams | 4.53 grams (1.9x dry weight) |
| Sample 99–309 Hydrocolloid foam w.10% alginate | 3.39 grams | 19.94 grams (5.9x dry weight) |

Results show that standard hydrophilic foam retains about 2x its own weight and hydrocolloid foam retains 3x to 8x its own weight depending on levels of hydrocolloid used.

We claim:

1. A medical dressing comprising a preformed hydrophilic polyurethane foam matrix having at least, one hydrocolloid absorptive agent integrally affixed and locked into and dispersed throughout said hydrophilic polyurethane foam matrix.

2. A medical dressing comprising:
   a hydrophilic polyurethane foam layer; said hydrophilic polyurethane layer comprising a preformed matrix from a polymerized composition of:
   (a) an aqueous mixture including water which is present in an amount from about 73% to about 99.6% by weight of the aqueous mixture and at least one hydrocolloid absorptive agent present in an amount of about 4% to about 26% by weight of the aqueous mixture; with
   (b) a hydrophilic polyurethane prepolymer of from about 25% to about 50% by weight of the total composition, and
   (c) said preformed matrix of the hydrophilic polyurethane foam layer having said at least one hydrocolloid absorptive agent affixed and locked into the matrix to improve the absorptive capacity of the formed hydrophilic polyurethane foam layer.

3. The medical dressing of claim 2, wherein said aqueous mixture further includes a surfactant.

4. A method for producing a medical dressing having at least one hydrophilic polyurethane composite foam layer consisting of the steps of:
   (a) forming an aqueous mixture having at least one hydrocolloid absorptive agent and water in a quantity sufficient for the mixture;
   (b) combining a hydrophilic urethane prepolymer with said aqueous mixture in a predetermined ratio to provide a polymerizing mixture for forming the matrix of the said at least one layer of hydrophilic polyurethane composite form, in which the hydrocolloid absorptive agent is integrally affixed and locked into the matrix and dispersed therethrough;
   (c) sizing said at least one layer of hydrophilic polyurethane composite foam; and
   (d) converting the foam layer into a desired shape for use.

5. A method of claim 4 wherein said aqueous mixture further includes a surfactant.

6. A method for producing a medical dressing according to claim 4 wherein the aqueous mixture further includes, at least one additive selected from the group consisting of medicaments, proteins, enzymes, nucleic acids, soaps, hemostatic agents, antibacterial, antifungal, odor management agents, disinfecting and sterilizing agents.

7. A method for producing a medical dressing according to claim 4 wherein said hydrocolloid absorptive agent is selected from the group consisting of gums, alginates, pectins, collagens, and gelatins.

8. A method for producing a medical dressing as in claim 4 wherein:
   (a) said hydrocolloid absorption agent is selected from the group consisting of gums, alginates, pectins, collagens and gelatins, and
   (b) the aqueous mixture further includes at least one additive from the group consisting of medicaments, proteins, enzymes, nucleic acids, soaps, hemostatic agents, antibacterial, antifungal, disinfecting and sterilizing agents.

9. A medical dressing comprising a preformed hydrophilic polyurethane foam matrix having, at least one hydrocolloid absorptive agent and at least one additive from the group consisting of medicaments, proteins, enzymes, nucleic acids, soaps, hemostatic agents, antibacterial, antifungal, disinfecting and sterilizing agents, integrally affixed locked into and dispersed throughout said hydrophilic polyurethane foam matrix.

10. The medical dressing of claim 1 or 9 wherein said at least one hydrocolloid absorptive agent is selected from the group consisting of gums, alginates, pectins, collagens, and gelatins.

11. The medical dressing of claim 1 or 9 wherein said at least one hydrocolloid absorptive agent is sodium alginate.

12. The medical dressing of claim 1 or 9 wherein said at least one hydrocolloid absorptive agent is calcium alginate.

13. The medical dressing of claim 1 or 9 wherein said at least one hydrocolloid absorptive agent is guar gum.

14. The medical dressing of claim 1 or 9 wherein said at least one hydrocolloid absorptive agent is locust bean gum.

15. The medical dressing of claim 1 or 9 wherein said at least one hydrocolloid absorptive agent is karaya gum.

16. The medical dressing of claim 1 or 9, wherein said medical dressing further includes a backing layer.

17. The medical dressing of claim 1 or 9, wherein said medical dressing further includes a pressure-sensitive adhesive layer.

* * * * *

UNITED STATES PATENT AND TRADEMARK OFFICE
CERTIFICATE OF CORRECTION

PATENT NO. : 6,566,576 B1  
DATED : May 20, 2003  
INVENTOR(S) : James F. Komerska, Michael J. Derr and Wayne Celia It is certified that error appears in the above-identified patent and that said Letters Patent is hereby corrected as shown below:

Column 1,
Line 43 "drying" should read -- dries --.
Line 54, "integrally dispersed" should read -- integrally affixed onto and dispersed --.
Line 55, "throughout the" should read -- throughout the urethane polymer matrix of --.

Column 2,
Line 36, "includes" should read -- include --.
Lines 44 and 45, after "thereby" delete "incorporated and".
Line 45, after "integrally" insert -- affixed or locked onto the urethane polymer --.
Line 45, after "integrally" delete "dispersed directly into the".
Line 46, after "foam" insert -- and generally uniformly dispersed therethrough --.

Column 4,
Line 59, after "follows" insert -- : --.

Column 5,
Line 12, "4.06" should read -- 4.00 --.
Lines 22 and 52, after "aqueous" insert -- mixture --.
Line 37, "was" should read -- were --.

Column 6,
Line 18, after "least" delete ",".

Signed and Sealed this

Eighteenth Day of November, 2003

JAMES E. ROGAN
*Director of the United States Patent and Trademark Office*